(12) United States Patent
Lamont

(10) Patent No.: US 7,155,276 B2
(45) Date of Patent: Dec. 26, 2006

(54) METHOD AND APPARATUS TO MODIFY CRANIAL ELECTRICAL POTENTIALS TO REMEDIATE PSYCHIATRIC DISORDERS AND TO ENHANCE OPTIMAL BRAIN FUNCTIONING

(76) Inventor: John Lamont, 23515 Brooks Rd., Chatsworth, CA (US) 91311

( * ) Notice: Subject to any disclaimer, the term of this patent is extended or adjusted under 35 U.S.C. 154(b) by 664 days.

(21) Appl. No.: 10/198,351

(22) Filed: Jul. 17, 2002

(65) Prior Publication Data

US 2003/0018366 A1    Jan. 23, 2003

Related U.S. Application Data

(60) Provisional application No. 60/305,883, filed on Jul. 17, 2001.

(51) Int. Cl.
*A61B 5/0482* (2006.01)
(52) U.S. Cl. .......................... 600/545; 607/45
(58) Field of Classification Search ............ 607/44–47, 607/139–141, 2, 9; 128/898; 600/545
See application file for complete search history.

(56) References Cited

U.S. PATENT DOCUMENTS

| | | | | |
|---|---|---|---|---|
| 3,709,228 A | * | 1/1973 | Barker | 607/139 |
| 3,896,790 A | * | 7/1975 | Dikmen | 600/383 |
| 4,503,863 A | * | 3/1985 | Katims | 600/554 |
| 4,640,290 A | * | 2/1987 | Sherwin | 600/382 |
| 4,967,038 A | * | 10/1990 | Gevins et al. | 600/383 |
| 5,342,410 A | * | 8/1994 | Braverman | 607/58 |
| 5,458,625 A | * | 10/1995 | Kendall | 607/46 |
| 5,540,736 A | * | 7/1996 | Haimovich et al. | 607/46 |
| 5,968,086 A | * | 10/1999 | Bonner et al. | 607/122 |
| 6,101,411 A | * | 8/2000 | Newsome | 604/20 |

FOREIGN PATENT DOCUMENTS

EP    0067922 A1 *  6/1981

* cited by examiner

*Primary Examiner*—George R. Evanisko
(74) *Attorney, Agent, or Firm*—Kelly Lowry & Kelley, LLP

(57) ABSTRACT

A method for modifying cranial electrical potentials utilizes an electrical lead having first and second electrodes. The electrical lead may also include either a resistive component for increasing the resistance of the electrical lead, or a diode for restricting the flow of electricity through the lead to a single direction. The electrical lead is attached between skin surface areas of a human head, such as between ears, or an ear and an area of the scalp or forehead. Preferably, two electrical leads are utilized, one lead extending from a left ear to a right portion of the head, and the other electrical lead extending from the right ear to the left portion of the head. Scalp electrical potentials are altered in a passive manner resulting in beneficial effects on a variety of psychiatric disorders and brain functioning.

11 Claims, 1 Drawing Sheet

METHOD AND APPARATUS TO MODIFY CRANIAL ELECTRICAL POTENTIALS TO REMEDIATE PSYCHIATRIC DISORDERS AND TO ENHANCE OPTIMAL BRAIN FUNCTIONING

RELATED APPLICATION

This application claims priority from U.S. Provisional Application No. 60/305,883 filed Jul. 17, 2001.

BACKGROUND OF THE INVENTION

The present invention generally relates to electrophysiology. More particularly, the present invention relates to instrumentation and methods for modifying cranail electrical potentials.

Several methods have been developed during and after the $19^{th}$ century to use electrical currents to improve mental health. In the mental health field, the most prominent of these is electroshock therapy, in which a current is sent between two electrodes, either bilaterally between the temporal areas, or unilaterally, between two electrodes at the right temporal area. The mechanism by which electroshock therapy operates is the induction of seizure activity in the brain. The most important advantages of this technique include remediation of otherwise refractory depression, and other disorders difficult to treat by chemotherapy or psychotherapy. The disadvantages include memory loss and possible destruction of brain tissue.

A second type of electrical therapy, cranial electrical stimulation, is currently in use for mental health disorders. In this treatment, a very small current is sent between electrodes connected to the ears or just behind the ears at the mastoid area. This therapy has been found useful with a variety of mental disorders including drug addiction, depression and anxiety. The advantages of this treatment include use with patients who are not amenable to verbal psychotherapy or who refuse medication. Disadvantages include the possibility of exacerbating intra cranial cancerous growths, and as yet unknown effects of introducing electrical current to the brain. The mechanism by which this method is considered to operate is via electrical effects on brain tissue, although the specific nature of such effects is unknown.

A third technique, which ostensibly induces change by means of operant conditioning of brainwaves, is called EEG Biofeedback, or neurotherapy. The measurement procedures in this treatment modality involve taking voltage measurements from the scalp. The measurement procedures induce a flow of current between the recording electrode(s) and a ground electrode on the body (usually the earlobe), and this results in changes in voltage potentials over the scalp. These changes appear to trigger electrical changes in the brain which are probably responsible for the positive results found with EEG biofeedback, rather than any operant conditioning of brainwave. EEG Biofeedback usually takes about fifteen to sixty sessions, each about thirty minutes long, during which continuous voltage measurements are taken from the scalp. The advantages of this technique include relatively lasting effects, the avoidance of drugs, and effectiveness with a wide range of disorders, some of which are not treatable with other modalities. Disadvantages include lengthy and costly treatment.

Accordingly, there is need for a method of electrophysiology which modifies cranial, electrical potentials without the need of introduction of electricity, and its accompanying disadvantages. There is also a need for an electrophysiology treatment which can be conducted in an efficient manner in order to avoid high costs. The present invention fulfills these needs and provides other related advantages.

SUMMARY OF THE INVENTION

The present invention alters cranial electrical potentials in a passive manner, by allowing biologically-generated currents to flow between points on the head and the body, resulting in beneficial effects on a variety of psychiatric disorders and brain functioning generally. The current is allowed to flow by simply connecting points on the head to points on the body (or between two cranial or two body points).

The method for modifying body electrical potentials in accordance with the present invention generally comprises the steps of attaching a first electrode of an electrical lead to a skin surface area of a human head. A second electrode of the electrical lead is attached to another skin surface of the human head. Electrical potentials of the head are passively modified to remediate psychiatric disorders and enhance optimal brain functioning.

Typically, either the first or second electrode comprises a conductive clip for attachment to an ear of the patient. Either the first or second electrode may comprise a conductive flat or cup-shaped electrode which can be attached via conductive paste to the appropriate skin surfaces. The flow of current may be impeded by some degree of resistance (depending upon the symptoms addressed), and may be restricted to flowing in one direction by the use of diodes.

A single electrical lead may be used with the first and second electrodes attached to the ears. Alternatively, one of the electrodes is attached to the ear area, and the other electrode is attached to either the scalp or forehead area. In a particularly preferred embodiment, two electrical leads are used. The first electrical lead extends between a left ear and a portion of the scalp or forehead right of the midline of the head. A second electrical lead extends from the right ear to a portion of the scalp or forehead left of the midline. A retentive member, such as a clip or headband, may be used for securely holding the electrodes in place on the scalp or forehead.

The apparatus and method for its use involve no use of external sources of electricity, and do not require any training beyond learning to attach electrodes at various points on the scalp and body.

Other features and advantages of the present invention will become apparent from the following and more detailed description taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

The present invention is considered to operate by means of its effect on the body's direct current electrical system. More specifically, the invention disrupts an electrical equilibrium of potentials of the body, and particularly over the head, forcing the body to reestablish the electrical equilibrium, together with any potentials within the brain controlled by them. It is believed that the direct current electrical system of the body controls or effects other systems, such as the endocrine system, all of which are known to effect psychological states. The reestablishing of scalp potentials in accordance with the present invention provides an opportunity to reestablish such in a more normal and healthy configuration.

Figure 1:
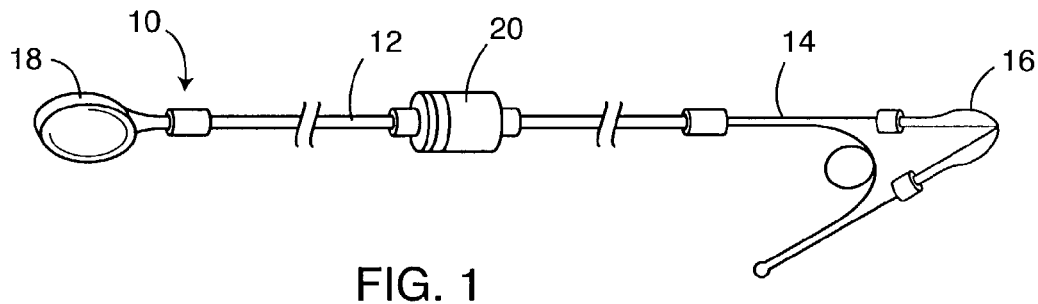
FIG. 1 is a partially fragmented perspective view of an electrical lead used in accordance with the present invention.

With reference now to FIG. 1, an electrical lead 10 utilized in accordance with the present invention is illustrated. Electrical lead 10 consists of a wire, preferably similar to those used in electroencephalography or those used in EEG biofeedback. One end of the wire has a first electrode 14 conductively attached thereto. The electrode 14 is typically comprised of a conductive metal, or metal plated with conductive material such as gold, silver or silver chloride. In a particularly preferred embodiment, as will be described more fully herein, the electrode 14 comprises a spring-loaded clip or the like. The clip 14 may have cup-shaped ends 16, as illustrated, in order to hold conductive paste. At the opposite end of the wire 12 is a second electrode 18 also comprised of a conductive metal or plated with conductive material. In a particularly preferred embodiment, the second electrode 18 is cup-shaped so as to hold conductive paste or cream to facilitate connection at the skin or scalp. However, the electrical lead 10 of the present invention may utilize adhesive electrodes which attach to the wire 12 using snaps, as are well-known in the art.

With continuing reference to FIG. 1, intermediate the ends of the wire 12 there may be an electrical component 20 such as a diode for restricting the flow of electricity to one direction only. Alternatively, or in addition, a resistive component such as an electronic resistor, may be inserted within the wire to provide a source of resistance ranging from negligible resistance to 100 megaohms to impede the flow of current along the electrical lead 10.

Figure 2:
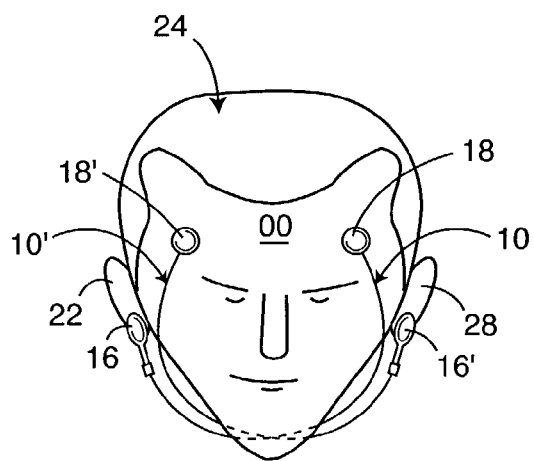
FIG. 2 is a schematic representation of a human head having two electrical leads positioned on skin surfaces thereof in accordance with the present invention.
Figure 3:
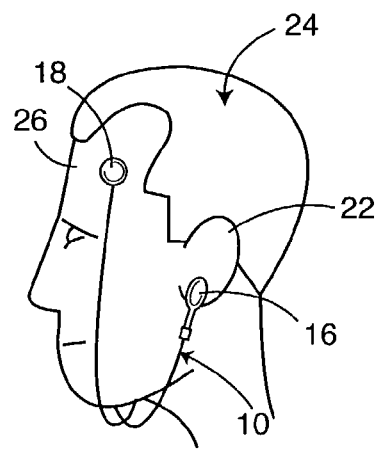
FIG. 3 is a side elevational view of FIG. 2.
Figure 4:
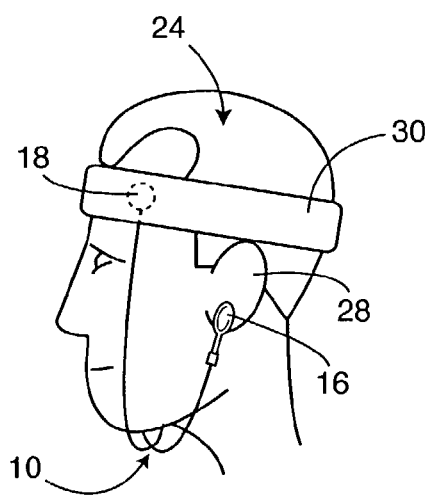
FIG. 4 is a side elevational view similar to FIG. 3, illustrating the use of a retentive member headband to hold electrodes of the electrical leads in place.

With reference now to FIGS. 2–4, in use, each electrical lead 10 is connected to points on the head or skin which are far enough apart to differ in voltage potential. In a particularly preferred embodiment, as shown in FIG. 2, two electrical leads 10 and 10' are used simultaneously and connected as follows. One electrode 16 of a first electrical lead 10 is clipped to the right ear 22 of the subject's head 24. The electrical lead 10 crosses under the chin and connects to a skin surface area on the upper forehead 26, preferably about two inches lateral to a midline of the head 24. The connection of the electrode 18 to the scalp or forehead can be made using ordinary electrode paste, or using snap-on electrodes containing a conductor. The second electrical lead 10' is similarly connected by connecting the clip electrode 16' to the left ear 28 and extending under the chin where the electrode 18' is attached at the opposite side of the forehead 26.

The voltage potential between the ear and scalp or forehead points (in the order of millivolts) is then allowed to dissipate. This often requires approximately 30 minutes. It has been found that there is a rise in voltage over the first 5 minutes, which dissipates thereafter. In order to secure the second electrodes 18 to the forehead or scalp, a retentive member 30 such as a headband or clip similar to those used in portable radios, is used.

Figure 5:
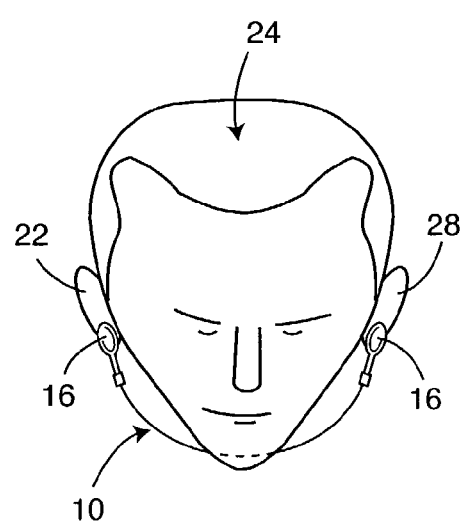
FIG. 5 is an elevational schematic view of an electrical lead extending between earlobes in accordance with the present invention.

With reference now to FIG. 5, some symptoms may require connection only between the two earlobes 22 and 28. In such instances, the electrical lead 10 has its electrodes 16 and 18 interconnected between the two earlobes 22 and 28. In such case, the electrodes 16 and 18 may both comprise spring-loaded clips or the like to facilitate such use. Alternatively, one or both of the electrodes 16 and 18 may be attached to the ears 22 and 28 with conductive paste, or snap-on electrodes adhered to the ears 22 and 28.

The device and method of the present invention is used for periods of time ranging from at least 5 minutes to about 1 hour. The preferred frequency and duration of this treatment of the present invention is once daily for 30 minutes until symptoms improve or remit. The number of sessions required varies with the type of disorder treated but is relatively small with disorders of mood and larger with developmental disorders such a autism or with attention deficit disorder.

The invention has been found to improve mood (particularly depression), normalize activity or arousal level (such as reducing attention deficit hyperactivity disorder), and to reduce oppositional behavior in children. It is believed that the device reduces aloofness and enhances social functioning in persons with autism. There is evidence that the device also functions to enhance optimal cognitive performance in persons without significant abnormalities of mood, arousal, cognition or behavior.

The current invention is safe, very inexpensive, requires little or no training and is a passive treatment. A passive treatment allows persons whose mental state precludes active participation in treatment to benefit from it. Such persons include the mentally disabled or severely disturbed, and children too young to actively take part in psychotherapy.

Although several embodiments of the present invention have been described in detail for purposes of illustration, various modifications of each may be made without departing from the spirit and scope of the invention. Accordingly, the invention is not to be limited, except as by the appended claims.

What is claimed is:

1. A method for modifying body electrical potentials, comprising the steps of:
   providing first and second electrical leads each having first and second electrodes;
   increasing the resistance of the leads using a resistive component;
   attaching the first electrode of the first lead to a skin surface area of a human head;
   attaching the second electrode of the first lead to another skin surface area on an opposite side of the human head;
   attaching the first electrode of the second lead to a skin surface area on the opposite side of the head as the first electrode of the first lead;
   attaching the second electrode of the second lead to another skin surface area on an opposite side of the human head as the first electrode of the second lead; and
   passively dissipating electrical potentials of the head to treat psychiatric disorders and brain functioning.

2. The method of claim 1, wherein the first or second electrode comprises a conductive clip.

3. The method of claim 1, wherein the first or second electrode comprises a conductive flat or cup-shaped electrode.

4. The method of claim 1, including the step of restricting the flow of electricity through the lead to a single direction using a diode.

5. The method of claim 1, wherein the first electrical lead extends from a left ear to a portion of the scalp or forehead right of a midline of the head, and the second electrical lead extends from a right ear to a portion of the scalp or forehead left of the midline.

6. The method of claim 1, including a retentive member for securely holding the second electrodes in place on the scalp or forehead.

7. A method for modifying body electrical potentials, comprising the steps of:

attaching a first electrode of a first electrical lead to a left ear of a human head, and attaching a second electrode of the first electrical lead to a skin surface area of the scalp or forehead right of a midline of the human head;

attaching a first electrode of a second electrical lead to a right ear of a human head, and attaching a second electrode of the second electrical lead to a skin surface area of the scalp or forehead left of the midline of the human head; and passively dissipating electrical potentials of the head to treat psychiatric disorders and brain functioning.

8. The method of claim 7, wherein the first electrode of the first and second leads comprises a conductive clip.

9. The method of claim 7, wherein the first or second electrode comprises a conductive flat or cup-shaped electrode.

10. The method of claim 7, including a retentive member for securely holding the second electrodes in place on the scalp or forehead.

11. The method of claim 7, including the step of increasing the resistance of the first and second electrical leads using a resistive component.

* * * * *